Dec. 2, 1958 H. C. SWIM Plant Pat. 1,776
ROSE PLANT
Filed Jan. 3, 1958
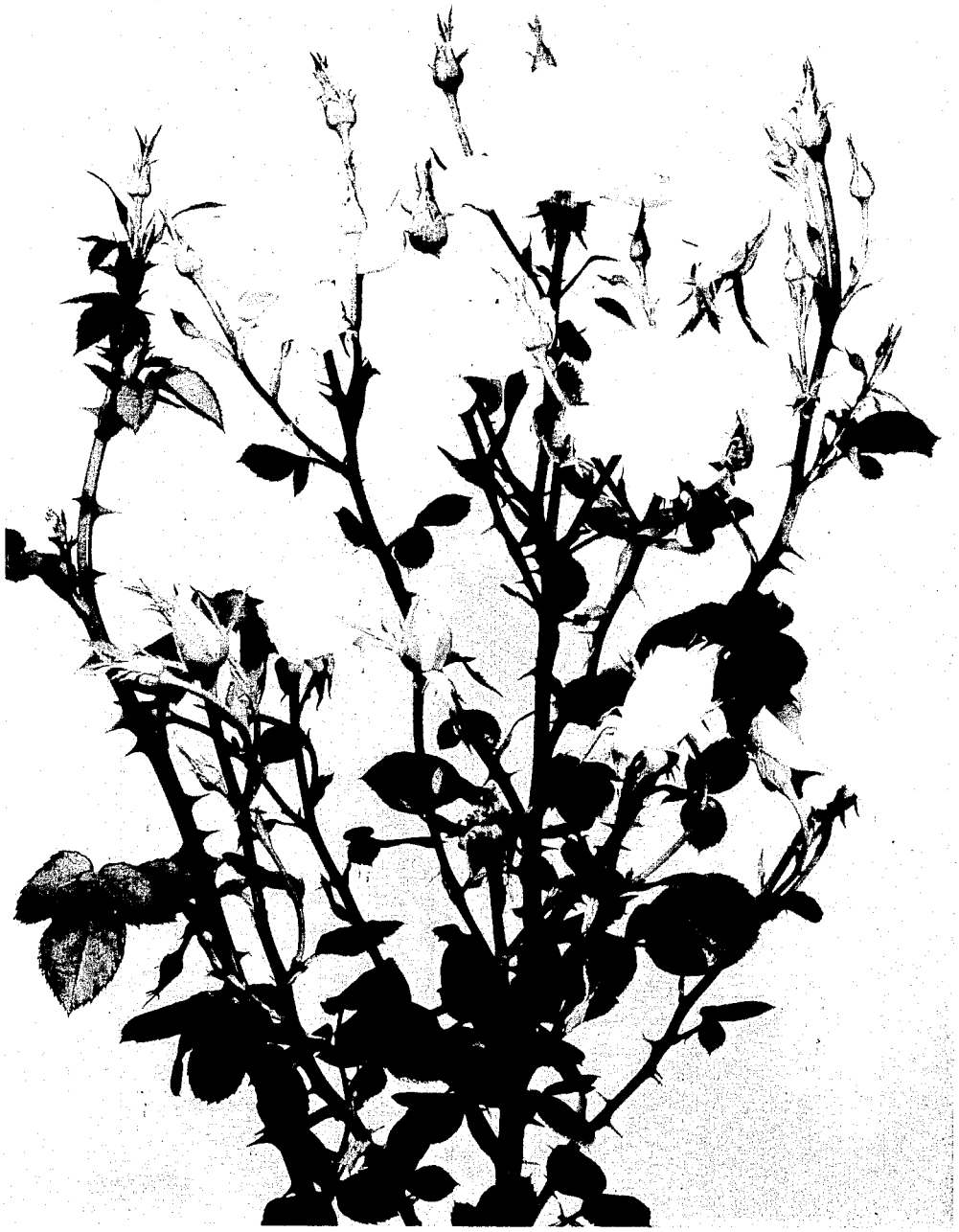
Inventor
H. C. Swim
By: Robert Robb
Attorneys United States Patent Office Plant Pat. 1,776
Patented Dec. 2, 1958

1,776

ROSE PLANT

Herbert C. Swim, Ontario, Calif., assignor to Armstrong Nurseries, Inc., Ontario, Calif., a corporation of California Application January 3, 1958, Serial No. 707,072

1 Claim. (Cl. 47—61)

The present invention relates to a new and distinct variety of rose plant of the hybrid polyantha class, which was originated by me by crossing the variety "Goldilocks" (Plant Patent No. 672) with an unnamed and unpatented variety, the latter being the pollen parent and the former being the seed parent.

The unnamed pollen parent was a rose of the floribunda type, which had an upright and moderately vigorous habit of growth, with its flowers borne in clusters of medium size, and each flower being of double form, from 3 to 4 inches in diameter, and of a light yellow color.

The primary objective of this breeding was to produce a new rose variety which combines the most desirable characteristics of the two parents. This objective was fully achieved, along with other improvements, as evidenced by the following unique combination of outstanding features which definitely differentiate the new variety from its parents, as well as from all other varities of which I am aware:

(1) Exceptional floriferousness, with better than average continuity of bloom;

(2) Semi-double flowers ranging from small to medium in size, with the flowers borne in clusters of from medium to large size; and (3) A bright yellow general color tonality of the flowers which fades relatively little before the petals drop, as compared with other yellow floribundas, and the general overall appearance being a brighter yellow than that of other yellow floribundas.

In comparison with its seed parent, "Goldilocks," the new variety has a semi-upright habit of growth, as distinguished from the spreading habit of "Goldilocks," and the flowers of the new variety are semi-double, rather than double like the flowers of this parent.

As compared with its pollen parent, the flowers of the new variety are slightly smaller, the flowers are semi-double, rather than double like those of this parent, and the flower color of the new variety is a darker yellow.

Asexual reproduction of my new variety by budding, as performed at Ontario, California, shows that the foregoing characteristics come true to form and are established and transmitted through succeeding propagations.

The accompanying illustration shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.
Class: Hybrid polyantha (floribunda).
Breeding: Seedling.
*Seed parent.*—"Goldilocks."

*Pollen parent.*—An unnamed seedling.
Propagation: Holds its distinguishing characteristics through succeeding propagations by budding.

*Flower*

Locality where grown and observed: Ontario, California.
Flowers borne: Usually from 3 to 5 or more to stem; in regular, rounded clusters; on stems of normal strength and medium length.
Quantity of bloom: Abundant, outdoors.
Continuity: Continuous during growing season.
Fragrance: Slight.
Bud:
*Peduncle.*—Average length; average caliper; erect; smooth; numerous gland-tipped cilia; few prickles. Color—near Buffy Brown, Plate XL (Ridgway) on side exposed to sun.
*Before calyx breaks.*—Size—small. Form—short; ovoid; with foliaceous appendages and few hairs on the surface of the bud; usually with slender, bristle-like foliaceous parts extending beyond the tip of the bud equal to ¼ or more of its length.
*As calyx breaks.*—Color—near Lemon Yellow, Plate 4, page 4 (Wilson).
*Sepals.*—Inner surface with fine, woolly tomentum; margins of alternate sepals lined with fine, woolly tomentum; others lined with gland-tipped cilia.
*As first petal opens.*—Size—small. Form—short; pointed; ovoid. Color: outside—near Aureolin, Plate 3/1, page 3 (Wilson); inside—near Aureolin, Plate 3, page 3 (Wilson).
*Opening.*—Opens up well; is not retarded from opening by cold, hot, wet or dry weather.
Bloom:
*Size (when fully open).*—From small to average; from 2¾ inches to 3 inches.
*Petalage.*—Semi-double; from 10 to 15 petals, plus from 2 to 4 petaloids; arranged regularly.
*Form.*—Somewhat high-centered at first, but becoming flat; petals being at first loosely flat, with lateral margins reflexed slightly, approximately ½ of the petal length, and with apex sometimes reflexed slightly, particularly on outer petals, becoming later at maturity somewhat more loosely flat, with lateral margins reflexed ¾ or more of the petal length, and with apex sometimes reflexed, particularly on outer petals.
Petals:
*Texture.*—Medium; leathery. Inside—satiny. Outside—satiny.
*Shape.*—Outside—broadly obovate, with apex flat, and sometimes with one or two notches. Intermediate—broadly obovate; sometimes with apex from rounded to flat, and with one or two notches. Inside—nearly round, with apex rounded, and sometimes with one or two notches.

This description of a newly opened flower was made from a rose grown outdoors in the month of October at Ontario, California:

*Color.*—Outer petal: outside surface—near Canary Yellow, Plate 2/2, page 2 (Wilson); inside surface—near Canary Yellow, Plate 2/2, page 2 (Wilson). Intermediate petal: outside surface—between Canary Yellow, Plate 2/2, page 2 (Wilson) and Canary Yellow, Plate 2/3, page 2 (Wilson); inside surface—near Canary Yellow, Plate 2/2, page 2 (Wilson). Inner petal: outside surface—between Canary Yellow, Plate 2/2, page 2 (Wilson) and Canary Yellow, Plate 2/3, page 2 (Wilson); inside surface—near Canary Yellow, Plate 2/2, page 2 (Wilson).

This description was made from a rose that was open for three days outdoors in the month of October, at Ontario, California:

*Color.*—Outer petal: outside surface—between Sulfur Yellow, Plate 1/3, page 1 (Wilson) and Canary Yellow, Plate 2/3, page 2 (Wilson); inside surface—between Canary Yellow, Plate 2/2, page 2 (Wilson) and Canary Yellow, Plate 2/3, page 2 (Wilson). Inner petal: outside surface—near Canary Yellow, Plate 2/1, page 2 (Wilson); inside surface—between Canary Yellow, Plate 2, page 2 (Wilson) and Canary Yellow, Plate 2/1, page 2 (Wilson).

*General color effect.*—Newly opened flower—between Aureolin, Plate 3, page 3 (Wilson) and Aureolin, Plate 3/1, page 3 (Wilson). 3-days open—between Canary Yellow, Plate 2/1, Page 2 (Wilson) and Canary Yellow, Plate 2/2, page 2 (Wilson).

*Behaviour.*—Drop off cleanly; not affected by cold, hot, wet or dry weather.

*Flower longevity.*—On bush in garden—from 3 to 5 days in October. Cut roses grown outdoors and kept at living-room temperatures—from 3 to 5 days in October.

*Reproductive organs*

Stamens: Many; regularly arranged about pistils.

Filaments: From short to medium length; from 3 to 9 mm. in length; many with anthers. Color—near Aureolin, Plate 3/1, page 3 (Wilson).

Anthers: Medium size; all open approximately at once. Color: upper side—margins near Cadmium Orange, Plate 8, page 8 (Wilson), with remainder near Lemon Yellow, Plate 4/2, page 4 (Wilson). Under side—margins near Cadmium Orange, Plate 8, page 8 (Wilson), with remainder near Lemon Yellow, Plate 4/2, page 4 (Wilson).

Pollen: Abundant. Color—near Indian Yellow, Plate 6/1, page 6 (Wilson).

Pistils: Many; approximately 50 in number.

Styles: Uneven; from short to average length; from 5 to 8 mm. in length; average caliper; bunched. Color: upper half—near Claret Rose, Plate 021/1, page 109 (Wilson); lower half—near Uranium Green, Plate 63/1, page 63 (Wilson).

Stigma: Color—near Empire Yellow, Plate 603/1, page 66 (Wilson).

Ovaries: Usually enclosed in calyx.

Hips: Short; globular; smooth; with walls thick and fleshy. Color (near maturity)—near Old Gold, Plate XVI (Ridgway).

Sepals: Permanent; medium length; recurved. Color: inside—near Light Elm Green, Plate XVII (Ridgway), lined with fine, woolly tomentum; outside—near Chromium Green, Plate XXXII (Ridgway).

Seeds: Few; from 8 to 10 in number; medium size.

*Plant*

Foliage:

*Leaves.*—Compound of usually 5 to 7 leaflets; from normal abundance to abundant; medium size; somewhat leathery; semi-glossy.

*Leaflets.*—Shape—ovoid, with apex acute; round base; margin simply serrate.

*Color.*—Mature: upper surface—near Leaf Green, Plate XLI (Ridgway); under surface—near Light Elm Green, Plate XVII (Ridgway). Young: upper surface—near Forest Green, Plate XVII (Ridgway); under surface—near Light Elm Green, Plate XVII (Ridgway).

*Rachis (the supporting stem of the compound leaf).*—Average size. Upper side—grooved; with some stipitate glands on edges. Under side—with 2 or 3 prickles.

*Stipules.*—Medium length; medium width; with medium length points turning out at an angle of more than 45°.

*Disease resistance.*—Better than average resistance to mildew as compared with other varieties grown under comparable cultural conditions at Ontario, California.

Growth:

*Habit.*—Bushy; semi-upright; much-branched.

*Growth.*—Free.

*Canes.*—Medium caliper.

*Main stems.*—Color—between Biscay Green, Plate XVII (Ridgway) and Light Elm Green, Plate XVII (Ridgway). Large prickles—several; from medium length to long; straight; with medium length, narrow base; color—between Clay Color, Plate XXIX (Ridgway) and Sayal Brown, Plate XXIX (Ridgway). Small prickles—none. Hairs—none.

*Branches.*—Color—near Biscay Green, Plate XVII (Ridgway). Large prickles—several; from medium length to long; almost straight; with medium length, narrow base; color—near Chrysolite Green, Plate XXXI (Ridgway). Small prickles—none. Hairs—none.

*New shoots.*—Color—near Parrot Green, Plate VI (Ridgway), sometimes overlaid lightly with near Buffy Brown, Plate XL (Ridgway). Large prickles—several; from medium length to long; almost straight; with medium length, narrow base; color—near Lime Green, Plate XXXI (Ridgway). Small prickles—none. Hairs—none.

I claim:

A new and distinct variety of rose plant of the hybrid polyantha class, substantially as herein shown and described, characterized particularly as to novelty by its floriferousness and better than average continuity of bloom, its semi-double flowers of from small to medium size and their habit of being borne in clusters of from medium to large size, and the distinctive bright yellow general color tonality of its flowers which remains substantially constant until the petals drop.

No references cited.